(12) United States Patent
Clark et al.

(10) Patent No.: US 12,324,621 B2
(45) Date of Patent: *Jun. 10, 2025

(54) CATHETER WITH IMPROVED IRRIGATED TIP ELECTRODE HAVING TWO-PIECE CONSTRUCTION, AND METHOD OF MANUFACTURING THEREFOR

(71) Applicant: BIOSENSE WEBSTER (ISRAEL) LTD., Yokneam (IL)

(72) Inventors: Jeffrey L. Clark, Castaic, CA (US); Daniel Gonzalez, La Verne, CA (US); John Thompson, San Clemente, CA (US); Ivan Totten, La Verne, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 5 days.

This patent is subject to a terminal disclaimer.

(21) Appl. No.: 18/486,429

(22) Filed: Oct. 13, 2023

(65) Prior Publication Data
US 2024/0032998 A1    Feb. 1, 2024

Related U.S. Application Data

(63) Continuation of application No. 17/090,886, filed on Nov. 5, 2020, now Pat. No. 11,819,266, which is a
(Continued)

(51) Int. Cl.
*A61B 18/14* (2006.01)
*A61B 17/00* (2006.01)

(52) U.S. Cl.
CPC .............. *A61B 18/1492* (2013.01); *A61B 2017/00526* (2013.01); *A61B 2218/002* (2013.01)

(58) Field of Classification Search
CPC ...... A61B 18/1492; A61B 2017/00526; A61B 2218/002
See application file for complete search history.

(56) References Cited

U.S. PATENT DOCUMENTS

| 4,819,048 A | 4/1989 | Mand et al. |
| 5,964,757 A | 10/1999 | Ponzi |

(Continued)

FOREIGN PATENT DOCUMENTS

| CN | 102232869 A | 11/2011 |
| EP | 1005839 A1 | 6/2000 |

(Continued)

OTHER PUBLICATIONS

Aloraier A., et al., "Role of Welding Parameters Using the Flux Cored Arc Welding Process of Low Alloy Steels on Bead Geometry and Mechanical Properties," Journal of Materials Engineering and Performance, Apr. 2011, vol. 21, pp. 540-547.

(Continued)

*Primary Examiner* — Michael F Peffley
*Assistant Examiner* — Bo Ouyang
(74) *Attorney, Agent, or Firm* — Etan S. Chatlynne; Calderon Safran & Wright P.C.

(57) ABSTRACT

A catheter has a two-piece tip electrode with a shell and a support structure that are secured to each other by multiple redundant mechanisms in order to reduce the risk of tip detachment during a procedure. The tip electrode includes at least two different welds attaching the shell to the support structure to provide a dual failure mode. One weld includes a seam weld and another weld includes a penetration weld.

19 Claims, 11 Drawing Sheets

Related U.S. Application Data continuation of application No. 13/958,455, filed on Aug. 2, 2013, now Pat. No. 10,828,089.

(56) References Cited

U.S. PATENT DOCUMENTS

| | | | |
|---|---|---|---|
| 6,120,496 | A | 9/2000 | Whayne et al. |
| 8,348,937 | B2* | 1/2013 | Wang ............... A61B 18/18 606/41 |
| 8,378,255 | B2 | 2/2013 | Nagashima et al. |
| 2004/0200813 | A1 | 10/2004 | Alips et al. |
| 2006/0171500 | A1 | 8/2006 | Pennington et al. |
| 2008/0091193 | A1* | 4/2008 | Kauphusman ..... A61B 18/1492 606/41 |
| 2008/0161791 | A1* | 7/2008 | Cao ............... A61B 18/1492 606/41 |
| 2008/0255540 | A1 | 10/2008 | Selkee |
| 2009/0093810 | A1 | 4/2009 | Subramaniam et al. |
| 2009/0125016 | A1 | 5/2009 | Wang et al. |
| 2010/0168827 | A1 | 7/2010 | Schultz |
| 2010/0176095 | A1 | 7/2010 | Chen et al. |
| 2011/0162195 | A1 | 7/2011 | Webster, Jr. et al. |
| 2011/0264089 | A1 | 10/2011 | Zirkle et al. |
| 2013/0123875 | A1* | 5/2013 | Varady ............... A61N 1/3968 607/36 |
| 2013/0253505 | A1 | 9/2013 | Schultz |

FOREIGN PATENT DOCUMENTS

| | | |
|---|---|---|
| EP | 1690510 A1 | 8/2006 |
| EP | 1690564 A1 | 8/2006 |
| EP | 2382935 A1 | 11/2011 |
| JP | H11347041 A | 12/1999 |
| JP | 2011505193 A | 2/2011 |
| JP | 2011229918 A | 11/2011 |
| JP | 2011229920 A | 11/2011 |
| JP | 2013059771 A | 4/2013 |
| RU | 2454965 C2 | 7/2012 |

OTHER PUBLICATIONS

European Search Report for European Application No. 14174896.2, mailed on Mar. 24, 2015, 7 pages.

* cited by examiner ively extending circumferentially around the tip electrode, and wherein each seam weld segment overlaps with at least one penetration weld segment.
CATHETER WITH IMPROVED IRRIGATED TIP ELECTRODE HAVING TWO-PIECE CONSTRUCTION, AND METHOD OF MANUFACTURING THEREFOR

CROSS-REFERENCE TO CO-PENDING APPLICATION

The present application is a Continuation Application under 35 U.S.C. § 120 of U.S. patent application Ser. No. 17/090,886, Nov. 5, 2020, which is a Continuation Application under 35 U.S.C. § 120 of U.S. patent application Ser. No. 13/958,455, filed Aug. 2, 2013, now U.S. Pat. No. 10,828,089. The entire contents of these applications are incorporated by reference herein in their entirety.

FIELD OF INVENTION

The present invention relates to electrophysiologic (EP) catheters, in particular, EP catheters for ablating cardiac tissue.

BACKGROUND

Ablation of cardiac tissue is well known as a treatment for cardiac arrhythmias. In radio-frequency (RF) ablation, for example, a catheter is inserted into the heart and brought into contact with tissue at a target location. RF energy is then applied through electrodes on the catheter to heat tissue to a destructive temperature in order to create a lesion for the purpose of breaking arrhythmogenic current paths in the tissue.

Irrigated catheters are now commonly used in ablation procedures. Irrigation provides many benefits including cooling of the electrode and tissue which prevents overheating of tissue that can otherwise cause adjacent blood to form char and coagulum. Irrigated tip electrodes are known, including tip electrodes with a two-piece construction having an inner support structure and a shell mounted thereon. A cavity is formed between the support structure and the shell to provide a plenum chamber that enables a more uniform flow of fluid exiting the tip electrode via fluid ports formed in the shell. However, the two-piece construction requires extra safety measures to minimize the risk of the shell detaching from the support structure while the tip electrode is in a patient's body.

Accordingly, it is desirable that a catheter with a two-piece tip electrode has at least a dual failure mode securing the shell and the support structure to each other to minimize the risk of shell detachment. Where the shell and support structure are welded to each other, it is desirable that the shell and support structure are attached by more than one independent weld of at least two different types of welds.

SUMMARY OF THE INVENTION

The present invention is directed to a catheter having a tip electrode with a mounted shell that is secured by multiple redundant mechanisms in order to reduce the risk of tip detachment during a procedure. The tip electrode includes at least two different welds attaching the shell to a tip support structure to provide a dual failure mode. One weld includes a seam weld and another weld includes a penetration weld.

In one embodiment, the catheter has an elongated catheter body, a control handle proximal of the catheter body, and a tip electrode distal of the catheter body, the tip electrode having a shell and a support member joined by a weld, the weld having at least one seam weld and at least one penetration weld.

In one embodiment, at least one seam weld and at least one penetration weld have an axial overlap and/or a circumferential overlap.

In one embodiment, the shell has a rim and the support structure has an annular ridge, and the tip electrode has a joint seam where the rim and the annular ridge are in contact with each other, and wherein the weld extends at least partially around the joint seam in a circumferential direction.

In one embodiment, the seam weld includes a butt weld between the rim and the annular ridge and the penetration weld includes a keyhole weld that extends through a wall of the rim and into a portion of the support structure.

In one embodiment, the seam weld includes at least one seam weld segment extending circumferentially around the tip electrode, and the penetration weld includes at least one penetration weld segment extending circumferentially around the tip electrode.

In one embodiment, the seam weld includes multiple seam weld segments extending circumferentially around the tip electrode and the penetration weld includes multiple penetration weld segments extending circumferent In a more detailed embodiment, the at least one seam weld has a circumferential overlap with an adjacent seam weld ranging between about 50% and 80%.

In a more detailed embodiment, the at least one seam weld and the at least one penetration have an axial overlap ranging between about 50% and 80%.

In a more detailed embodiment, adjacent seam weld segments and penetration weld segments have a relative circumferential overlap ranging between 5-15 arc lengths.

In a more detailed embodiment, the at least one seam weld spans axially across the seam, and the at least one penetration weld radially penetrates through a wall of the shell and into the support structure.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
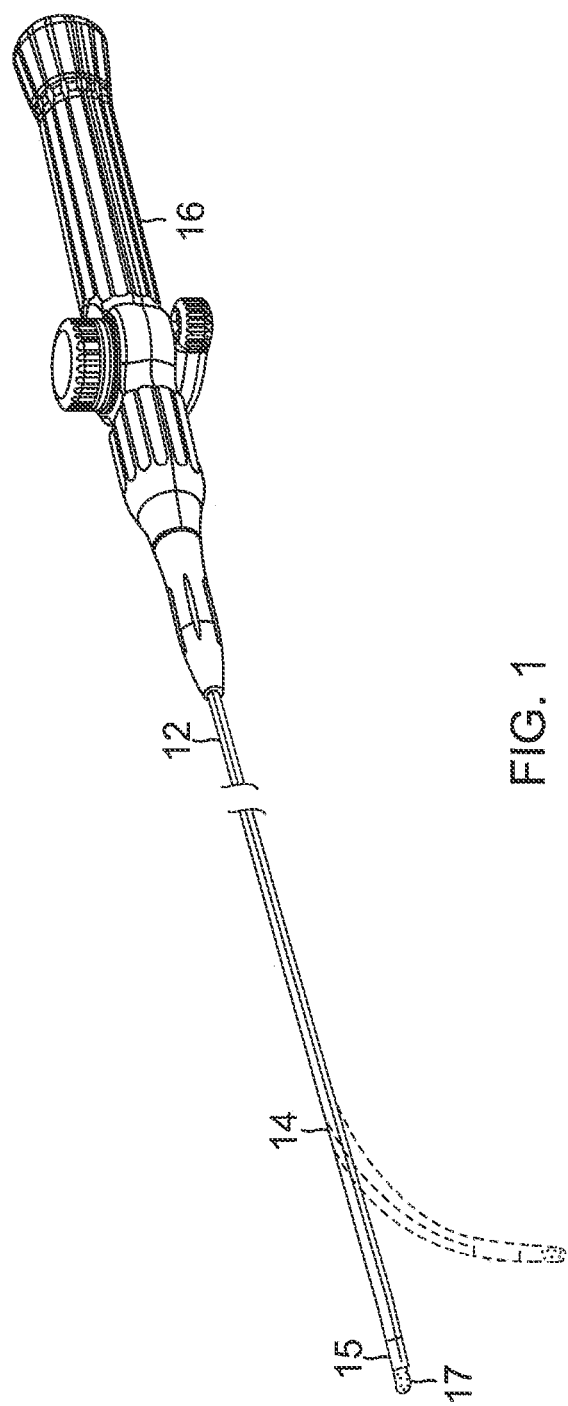
FIG. 1 is a perspective view of catheter in accordance with an embodiment of the present invention.

FIG. 1 illustrates an embodiment of a catheter 10 with a 2-piece irrigated ablation tip electrode with redundant attachment mechanisms. The catheter has an elongated catheter body 12 with proximal and distal ends, an intermediate deflectable section 14 at the distal end of the catheter body 12, and a distal section 15 with a tip electrode 17. The catheter also includes a control handle 16 at the proximal end of the catheter body 12 for controlling deflection (single or bi-directional) of the intermediate section 14 relative to the catheter body 12.

Figure 2A:
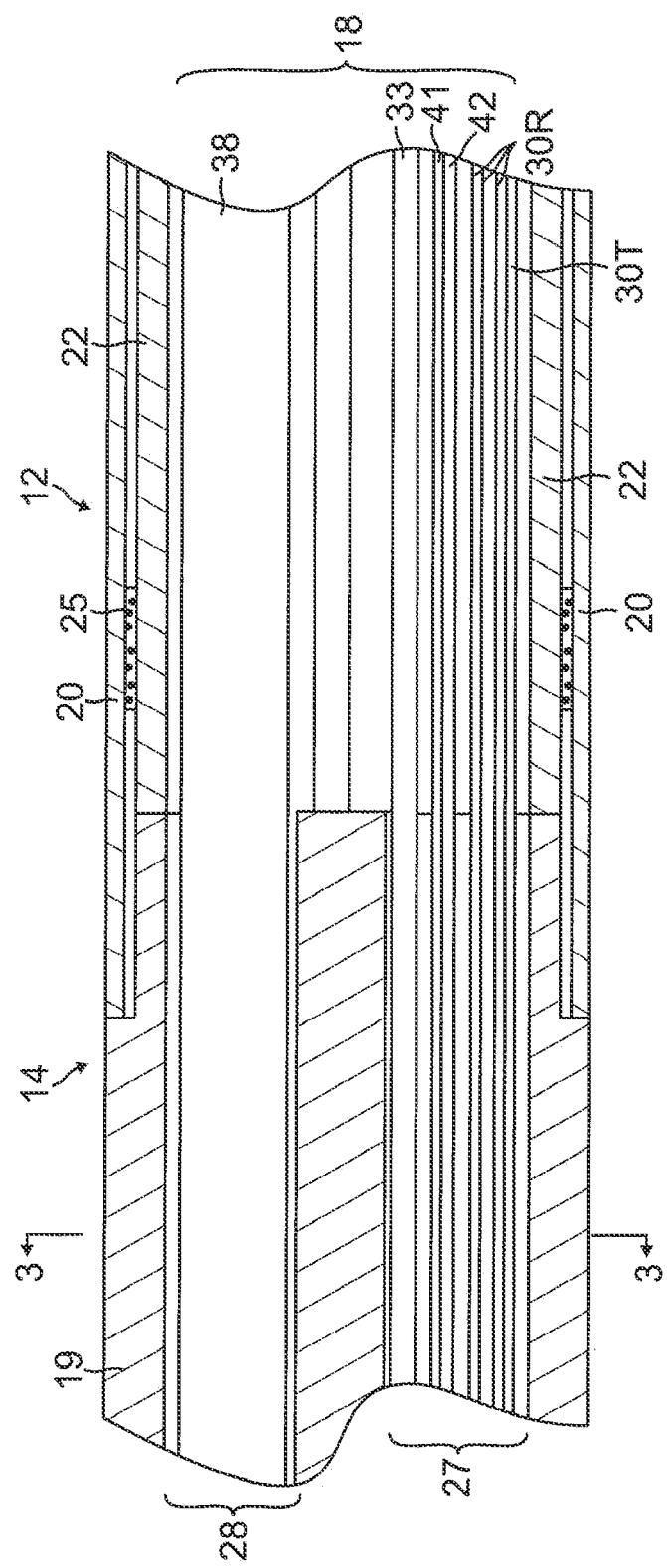
FIG. 2A is a side cross-sectional view of a junction between a catheter body and an intermediate deflection section along a first diameter, in accordance with an embodiment of the present invention.
Figure 2B:
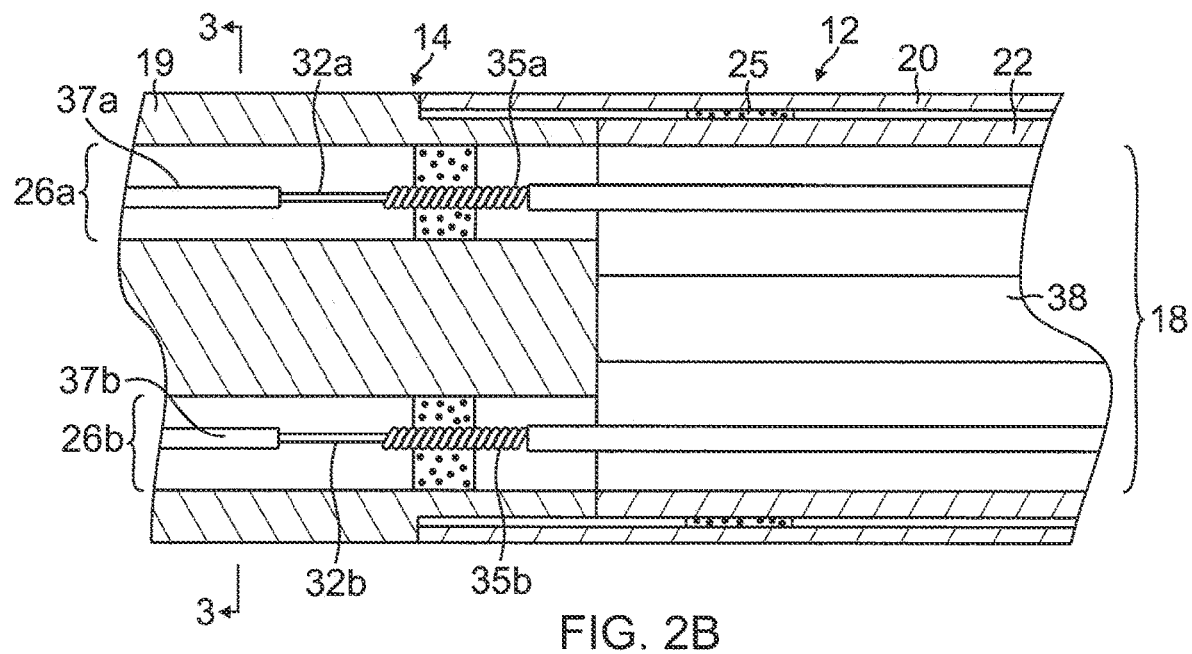
FIG. 2B is a side cross-sectional view of the junction of FIG. 2A taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint (not shown) is formed between proximal ends of the stiffening tube 22 and outer wall 20 using a slower drying but stronger glue, e.g., polyurethane.

Components that extend between the control handle 16 and the deflectable section 14 pass through the central lumen 18 of the catheter body 12. These components include lead wires 30T and 30R for the tip electrode 17 and a plurality of ring electrodes 21 carried on the distal section 15, an irrigation tubing 38 for delivering fluid to the tip electrode, a cable 33 for an electromagnetic position sensor 34 carried in the distal section 15, puller wires 32a, 32b for deflecting the intermediate section 14, and a pair of thermocouple wires 41, 42 to sense temperature at the distal section 15.

Figure 3:
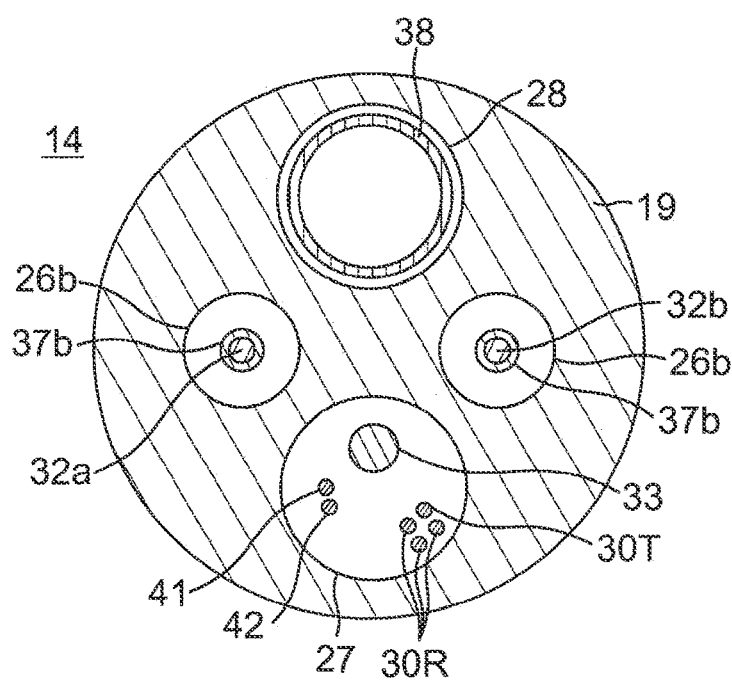
FIG. 3 is an end cross-sectional view of the intermediate deflection section of FIGS. 2A and 2B, taken along line A-A.

Illustrated in FIGS. 2A, 2B and 3 is an embodiment of the intermediate section 14 which comprises a short section of tubing 19. The tubing also has a braided mesh construction but with multiple lumens, for example off-axis lumens 26a, 26b, 27, 28. The first lumen 26a carries a puller wire 32a for deflection of the intermediate section. For bi-directional deflection, the diametrically opposing second lumen 26b carries a second puller wire 32b. The third lumen 27 carries the lead wires 30T and 30R, the thermocouple wires 41 and 42, and the sensor cable 33. The fourth lumen 28 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 25 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 32a and 32b is preferably coated with Teflon®. The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, portion of each puller wire in the catheter body 12 passes through a compression coil 35 in surrounding relation to its puller wire. Each compression coil 35 extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is preferably slightly larger than the diameter of the puller wire. Each portion of the puller wires distal of the compression coil 35 may extend through a respective protective sheath 39 to prevent the puller wire from cutting into the tubing 19 of the intermediate section 14 during deflection.

Proximal ends of the puller wires 32a and 32b are anchored in the control handle 16. Distal ends of the puller wires 32a and 32b are anchored in the distal section 15, as described further below. Separate and independent longitudinal movements of the puller wires relative to the catheter body 12, which results in, respectively, deflection of the intermediate section 14 along a plane, are accomplished by suitable manipulation of a deflection member of the control handle 16. Suitable deflection members and/or deflection assemblies are described in co-pending U.S. Publication No. US2010/0168827 A1, published Jul. 1, 2010, entitled DEFLECTABLE SHEATH INTRODUCER, and U.S. Publication No. US2008/0255540 A1, published Oct. 16, 2008, entitled STEERING MECHANISM FOR BI-DIRECTIONAL CATHETER, the entire disclosures of both of which are hereby incorporated by reference.

Figure 7:
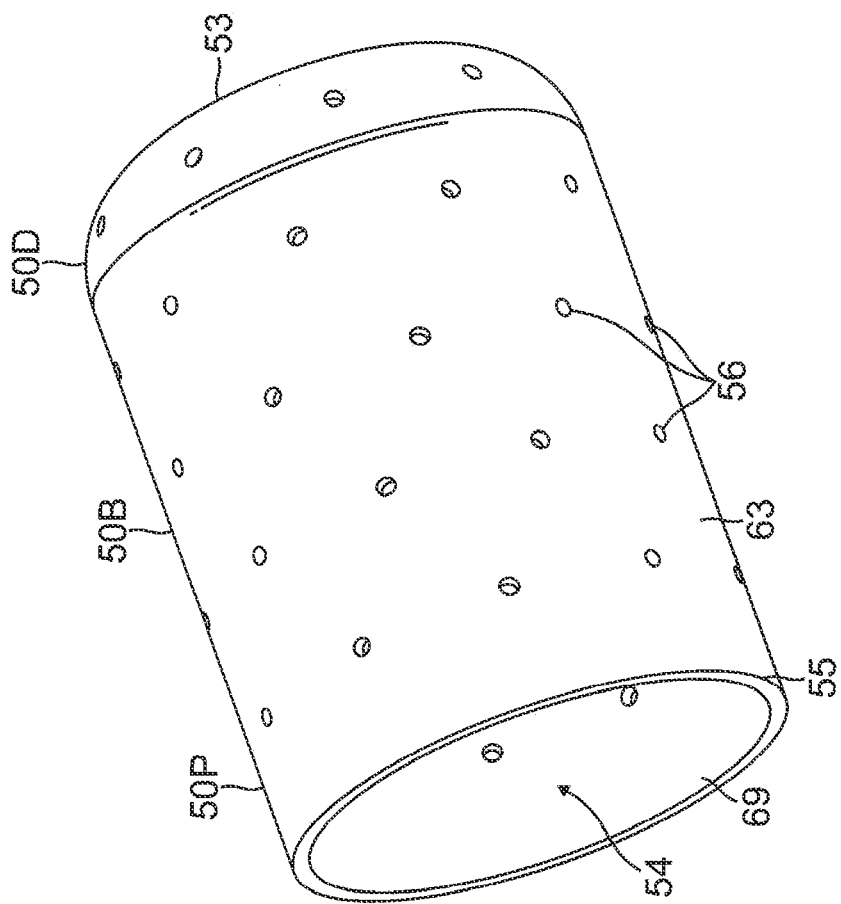
FIG. 7 is a perspective view of the shell of FIG. 6.

With reference to FIG. 7, at the distal end of the intermediate section 14 is the distal tip section 15 that includes the tip electrode 17 and a relatively short piece of non-conductive connector tubing or covering 24 between the tip electrode 17 and the intermediate section 14. In the illustrated embodiment, the connector tubing 24 has a single lumen 44 which houses the position sensor 34 and allows passage of components including electrode lead wires 30T and 30R, the sensor cable 33, thermocouple wires 41 and 42, and the irrigation tubing 38 into the distal section 15 and tip electrode 17. The single lumen 44 of the connector tubing 24 allows these components to reorient themselves as needed from their respective lumens in the intermediate section 14 toward their location within the distal section 15 and tip electrode 17. In the disclosed embodiment, the tubing 24 is a protective tubing, e.g., PEEK tubing, having a length ranging between 6 mm and 12 mm, more preferably about 11 mm.

Figure 6:
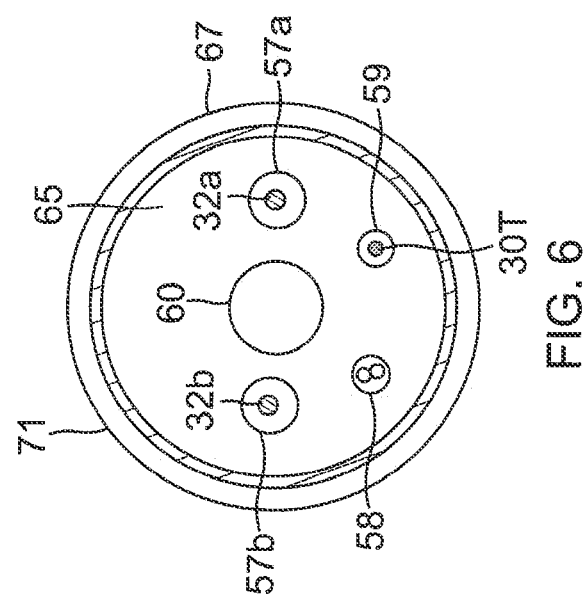
FIG. 6 is an end cross-sectional view of the tip electrode of FIG. 5, taken along line A-A
Figure 8:
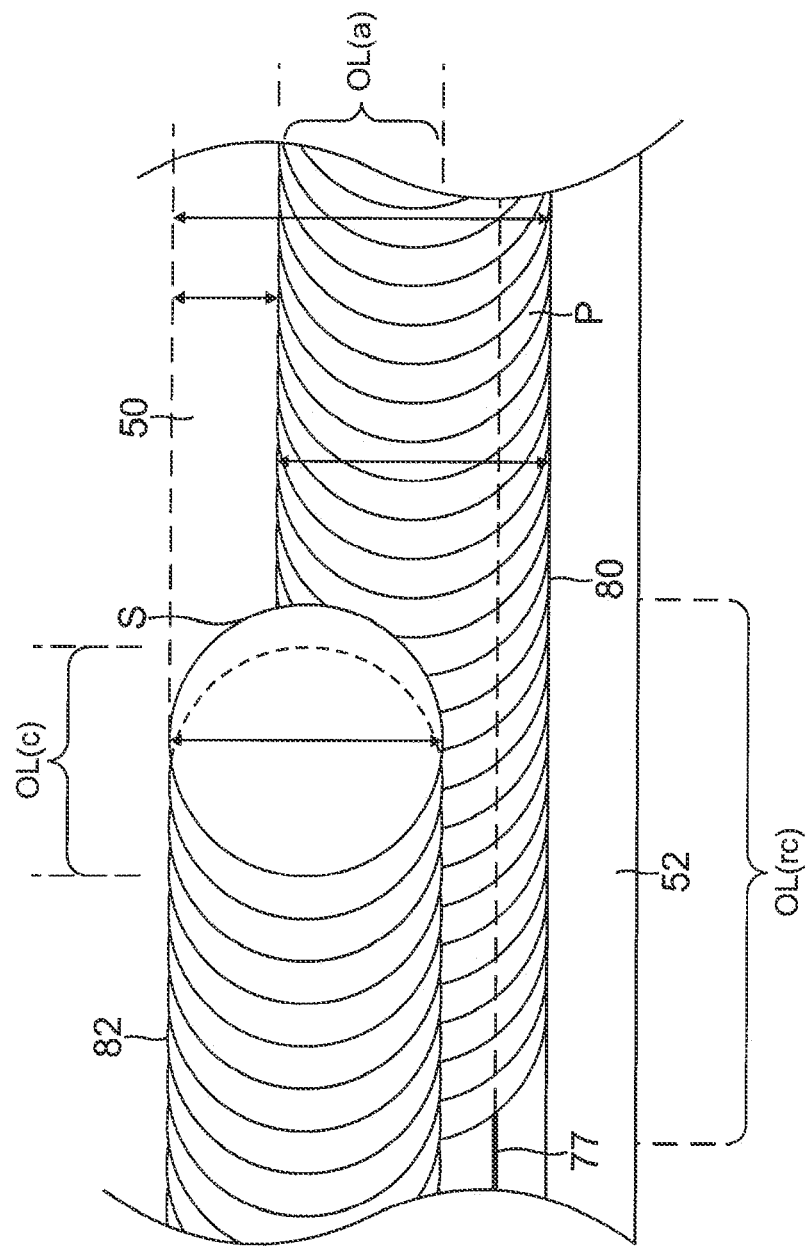
FIG. 8 is a detailed view of a seam weld segment and a penetration weld segment of the tip electrode of FIG. 4.

With reference to FIGS. 6, 7 and 8, the irrigated tip electrode has a two-piece construction that includes an electrically-conductive dome shell 50 and an electrically-conductive internal support member 52 which jointly define a cavity of an internal plenum chamber 51 that is surrounded and enclosed by the shell 50 and the support member 52. The shell 50 has a hollow cylindrical body 50B with an open nonablating proximal portion 50P and a closed ablating distal portion 50D adapted for tissue contact. The distal portion 50D has a domed atraumatic distal end 53. The proximal portion 50P has an open proximal end 54 defined by a peripheral rim 55. Formed in shell wall 63 are a plurality of fluid ports 56 that allow fluid communication between the cavity 51 and outside the shell 50.

The support member 52 forms a fluid-tight seal with the proximal end 54 of the shell 50 at visible or joint seam 77. The support member 52 seals the interior cavity 51 of the shell 50, and the shell 50 and the support member 52 facilitate the provision of a plenum condition within the cavity; that is, where fluid is forced or delivered into it for a more uniform distribution through fluid ports 56 formed in shell wall 63.

The support member 52 has a generally cylindrical body with a distal portion 52D and a proximal portion 52P. The distal portion 52D has a smaller diameter for extending into the cavity of the shell 50, and the proximal portion 52P has a larger diameter which is sized for an interference fit in the proximal end 54 of the shell 50. On an outer surface 68 of the proximal portion 52P, an annular ridge 67 is provided to abut against a proximal surface of the rim 55 of the shell 50. The proximal portion 52P also includes a generally tubular portion 61 for insertion into and connection with a distal end of the deflectable section 14 of the catheter 10. The ridge 67 has a height H that corresponds with a thickness T of the shell wall 63 so that a smooth outer profile is provided at the visible seam joint 77 between the rim 55 and the ridge 67 when the shell 50 is mounted on the support member 52. The ridge 67 is located a predetermined distance D proximal of the distal end of the proximal portion 52P so that the outer surface 68 contacts an inner surface 69 of the shell 50 immediately distal of the rim 55.

As shown in FIG. 6, the proximal portion 52P of the support member 52 has a plurality of axial holes. In the illustrated embodiment, proximal surface 65 of the proximal portion 52P has four blind holes, namely, 57a, 57b, 58 and 59, and one through-hole 60. The blind holes 57a and 57b are off-axis, diametrically opposed and in longitudinal alignment with lumens 26a and 26b of the deflectable section 14 for receiving and anchoring the puller wire(s). The blind hole 58 is off-axis and adapted to receive and anchor distal ends of thermocouple wires 41/42. The blind hole 59 is off axis and adapted to receive and anchor a distal end of tip electrode lead wire 30T. The through-hole 60 is on-axis and adapted to receive a distal end of irrigation tubing 38.

Figure 5:
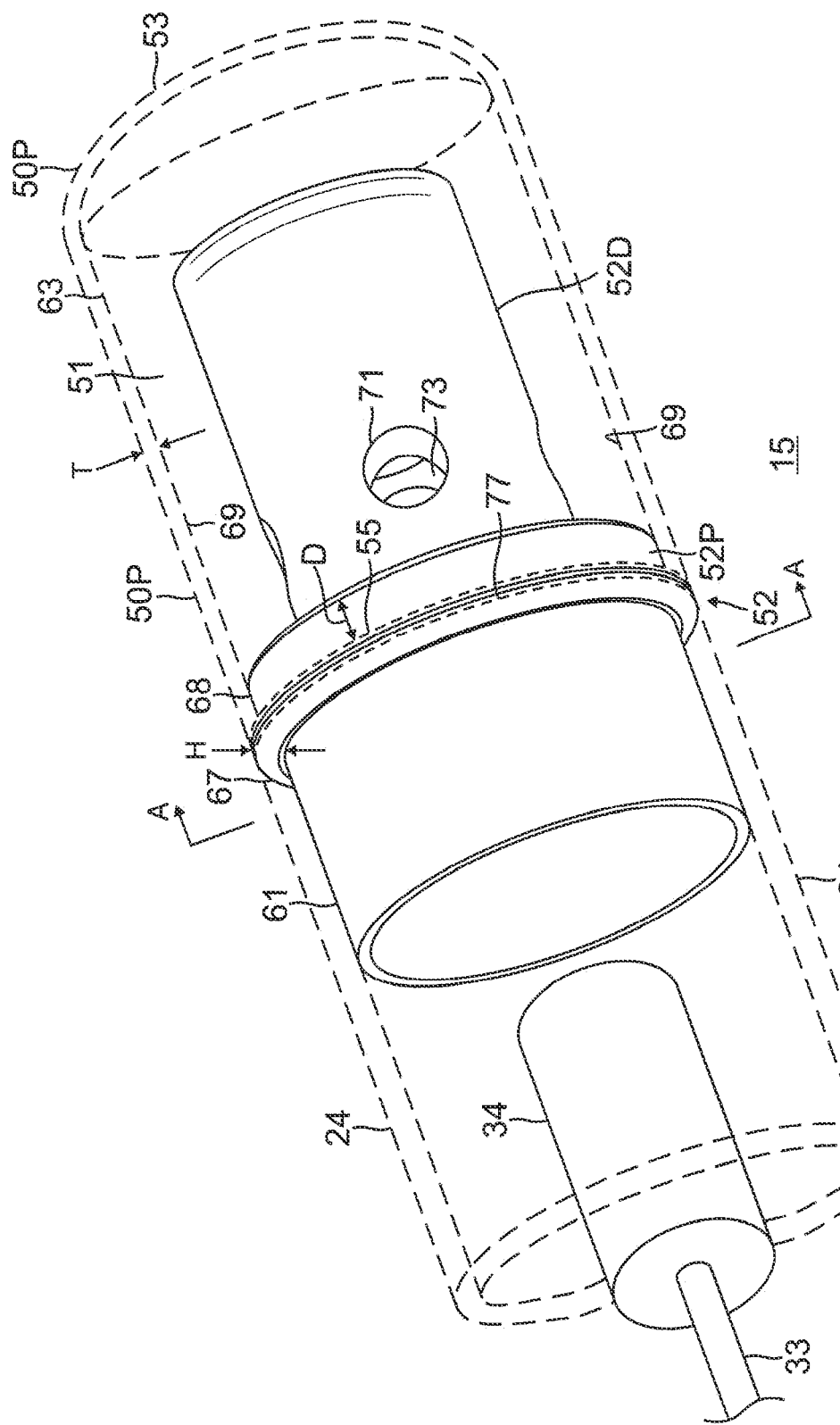
FIG. 5 is a perspective view of the tip electrode of FIG. 6, with the shell shown in transparency.

The through-hole 60 extends through the proximal portion 52P and feeds into and connects with a fluid channel 73 (FIG. 5) formed in the distal portion 52D. The channel 73 communicates with a plurality of fluid ports 71 formed in the distal portion 52D which allows fluid to enter the cavity 51 of the tip electrode and exit to outside of the tip electrode via fluid ports 56.

The shell 50 and the support member 52 are constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell 50 and the member 52 are constructed of an alloy comprising about 90% platinum and about 10% iridium by weight. The shell can formed by deep-drawing manufacturing process which produces a sufficiently thin but sturdy shell wall that is suitable for handling, transport through the patient's body, and tissue contact during mapping and ablation procedures.

Figure 4:
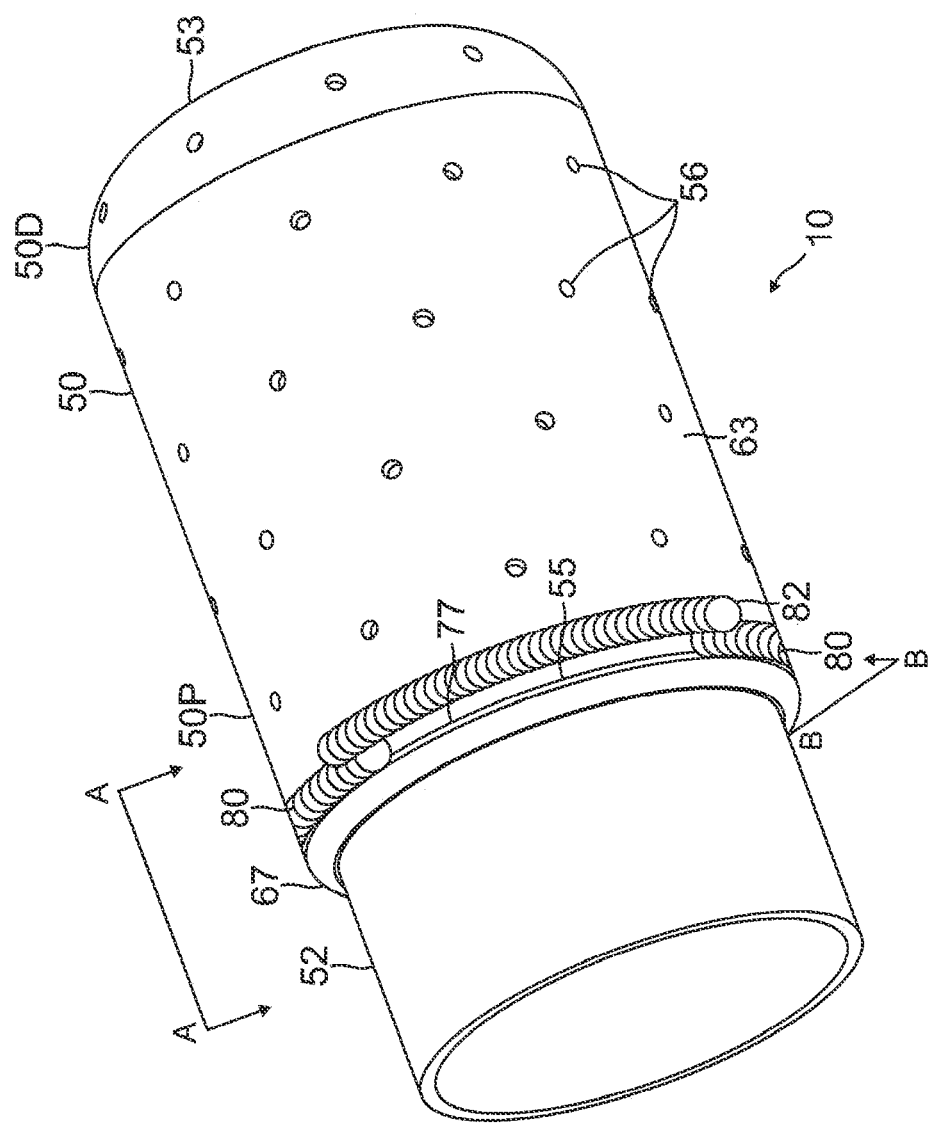
FIG. 4 is a perspective view of a tip electrode with a shell and a support structure, in accordance with an embodiment of the present invention.

As shown in FIG. 4, the shell 50 is mounted on the support member 52 with the rim 55 and the annular ridge abutting each other to form the visible seam 77 that extends circumferentially around the tip electrode. The shell and the support member are fixedly joined to each other by laser beam welding (LBW), a welding technique used to join metal through the use of a laser. The beam provides a concentrated heat source, resulting in small heat-affected zones. In accordance with a feature of the present invention, the shell 50 and the support member 52 are joined by at least two independent laser welds with circumferential and axial overlap that provide multiple (e.g., dual) failure mode. In the illustrated embodiment, one weld is a seam (or conduction) weld 80 and another weld is a penetration (or keyhole) weld 82. The seam weld 80 is performed at a lower energy density to form a series of weld nuggets, each of which is shallow and wide. The penetration weld 82 is performed at a power density to form a series of weld keyholes that extends deeper so as to penetrate through the shell wall and into the support member.

Figure 11:
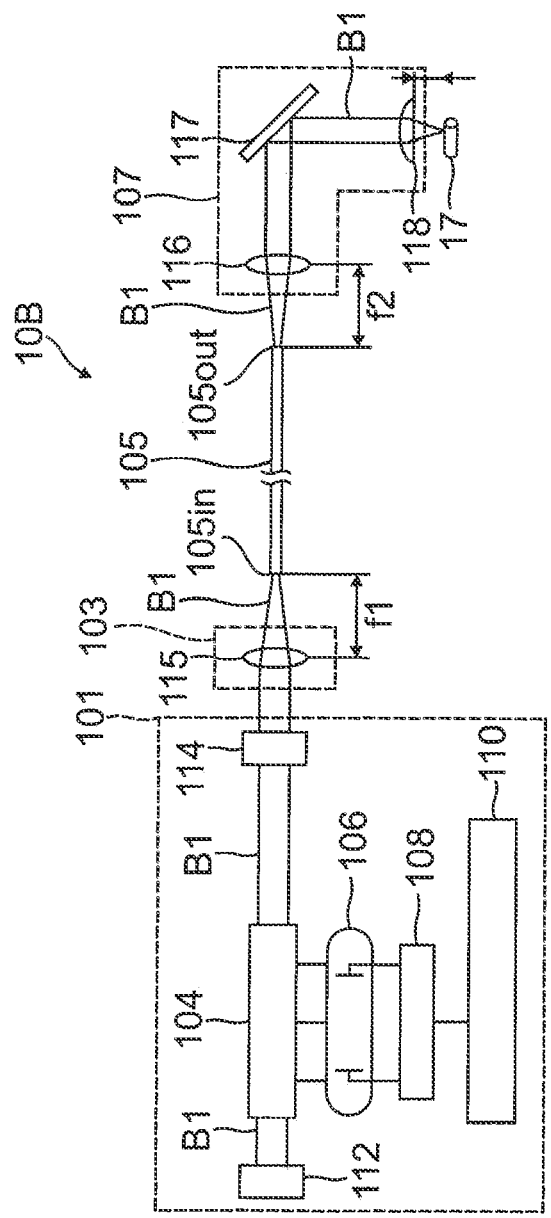
FIG. 11 shows a concept of a laser beam irradiation apparatus according to an embodiment.
Figure 12:
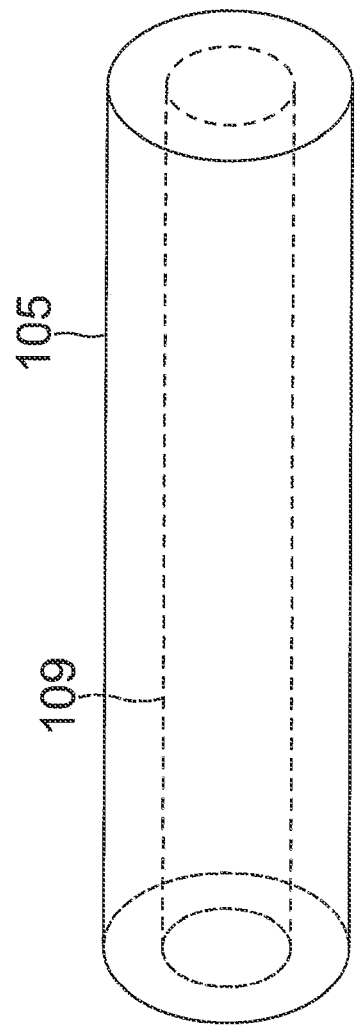
FIG. 12 is a perspective view showing an optical fiber of the apparatus of FIG. 11.

In the embodiment of FIG. 11, a laser beam irradiation apparatus 100 for welding the shell and the support structure includes a laser beam generator 101, such as a gas laser or a solid state laser, and an optical assembly 102. The solid state laser may include an Nd:YAG rod 104, a flash lamp 106, a power supply 108, a controller 110, a total reflection mirror 112 and an output mirror 114. The controller 110 controls lighting pulses of the flash lamp 106 through the power supply 108 so as to generate pulse YAG laser beams B. Optical fiber 105 has a circular core 109 (FIG. 12) providing a laser beam spot S with a circular cross-section, as shown in FIG. 4. The optical assembly 102 may include an incident optical unit 103, an optical fiber 105 and an emission optical unit 107.

The power supply 108 is connected between the flash lamp 106 and the controller 110. Electric power is supplied by the controller 110 from the power supply 108 to the flash lamp. Through the power supply 108, the controller 110 controls the output of the laser beam generator 101 and the properties of the laser beam B.

The total reflection mirror 112 is positioned a predetermined distance from a proximal end of the rod 104 so that any laser beam B outputted from the proximal end of the rod is reflected back to the proximal end. The output mirror 114 is positioned a predetermined distance from a distal end of the rod 104. The output mirror 114 is semi-transparent so that only a solid laser beam B from the rod 104 is allowed to pass through.

The incidental optical unit 103 including a condensing lens 115 with focal length f1 focuses the laser beam B outputted from the output mirror 114 onto an input end 105$in$ of the fiber optic 105.

The optical fiber 105 is an optical waveguide for transmitting laser beam B, by using a core 109 provided therein. The optical fiber 105 is provided between the incidental optical unit 103 and the emission optical unit 107 which receives the laser beam B from an output end 105$out$ of the fiber optic 105. The emission optical unit 107 irradiates the tip electrode 17 with the laser beam B emitted from the output end of the fiber optic 105. The emission optical unit 107 includes a collimator lens 116 and an angled mirror 117 and a light-emission lens 118. The collimator lens 116 is positioned at predetermined distance of its focal length f2 from the output end of the fiber optic 105. A suitable laser beam irradiation apparatus is described in U.S. Pat. No. 8,378,255, the entire disclosure of which is incorporated herein by reference.

As understood by one of ordinary skill in the art, the weld created by each pulse is determined by peak power density and pulse duration. The number of pulses per second, pulse overlap and welding speed also define a seam weld. In that regard, peak power density controls weld penetration and is a function of the fiber type and core diameter, focus optics, and laser peak control output. Pulse width controls the heat into the part, weld width and thermal heat cycle. Pulse repetition rate or pulse frequency also controls the heat into the part and thermal heat cycle. Pulse spacing is controlled by laser spot size, pulse frequency, and rotational speed of the support member and the shell mounted thereon. The size (e.g., diameter) of laser spot S (e.g., about 0.010 inch) is depends on the core diameter and is controlled by a weld schedule executed by the respective controllers and the focal length of the respective optical units. Laser welding parameters are stored as weld schedules within each controller. Focus settings are controlled by a focus knob micrometer on the seam weld laser optical unit and the penetration weld laser optical unit.

With reference to FIG. 4, each of the seam weld 80 and the penetration weld 82 is performed with a predetermined circumferential overlap OL(c) of the laser beam circular spot S at a relatively high value, ranging between about 50-90%, and preferably between about 70-80%. For purposes of discussion, a plurality of such overlapping spots S forms a segment, and one or more segments forms a seam weld or a penetration weld.

Figure 9A:
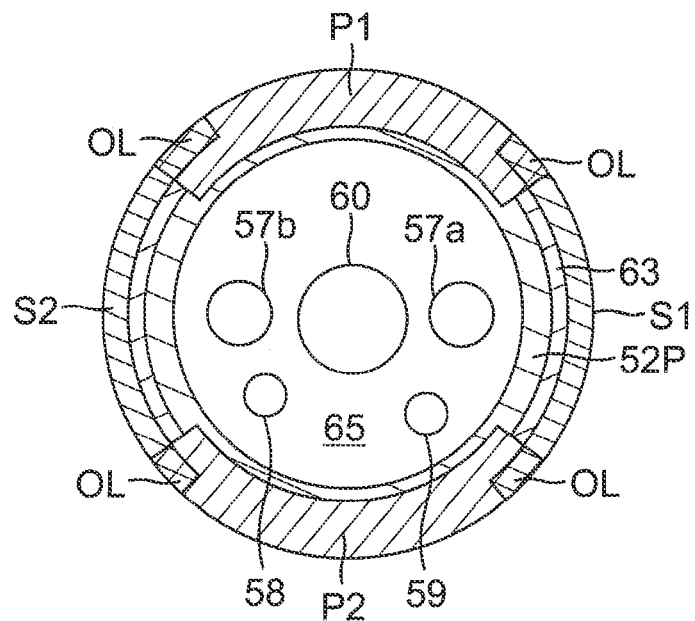
FIG. 9A is an end cross-sectional view of the tip electrode of FIG. 4, taken along line B-B.

The seam weld 80 welds together the visible seam joint 77 (or "butt" joint) between the rim 55 of the shell 50 and the annular ridge 67 of the support member 52. In the illustrated embodiment, the laser beam spot S is positioned over the seam 77 to axially overlap at least a portion of the rim 55 and at least a portion of the ridge 67. The seam weld 80 may comprise a plurality of circumferentially-extending discontinuous segments S1-Sn. In the illustrated embodiment of FIG. 9A, n=2 such that the seam weld 80 includes a first segment S1 and a second segment S2, with each segment being diametrically opposed to each other and extending between about 90-110 degrees, and preferably about 100 degrees, in arc length. In the illustrated embodiment of FIG. 9B, n=4 such that the seam weld 80 includes segments S1-S4, each at equidistance from adjacent segments and having the same circumferential length. The four segments form two pairs, each segment of a pair being diametrically opposed from its mate. It is understood that n at a minimum is 2 and may have a maximum that is equal to the total sum of the number of seam and penetration segments around the circumference divided by 2.

Figure 10:
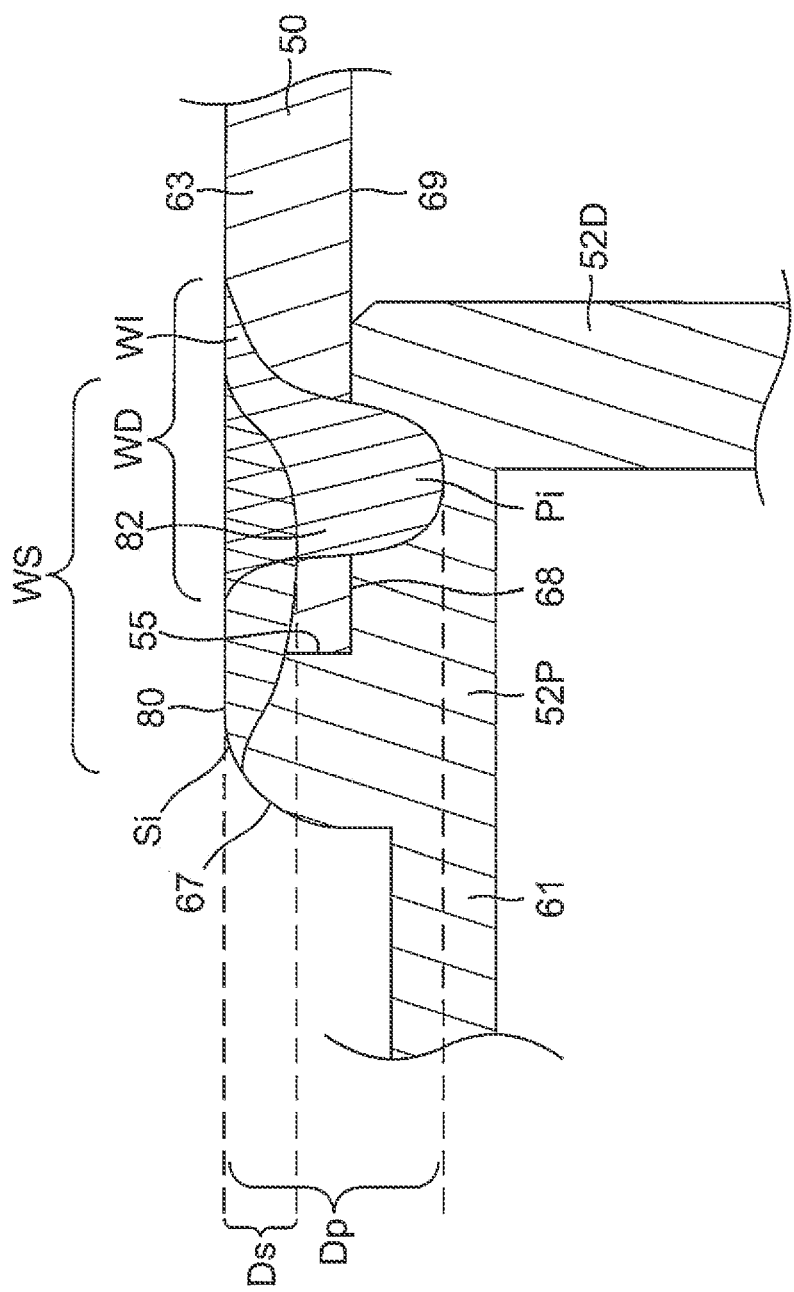
FIG. 10 is a side cross-sectional view of the tip electrode of FIG. 4, taken along line A-A.

As shown in FIG. 10, the rim 55 and the ridge 67 are welded in an axially side-by-side configuration by a seam weld segment Si, each of which has a weld depth DS that is generally equal in both the ridge 67 of the support member 52 and the shell wall 63 of the shell 50. As understood by one of ordinary skill in the art, each seam weld segments Si has an axial width Ws (as each laser spot S has a diameter Ws) that sufficiently spans across and straddles the ridge 67 and the rim 55. Lateral tolerance is important to assure that the position of the visible seam 77 under the laser beam is precise enough so that the laser beam does not miss the visible seam 77 while the shell 50 and the support structure 52 are rotated under the laser beam B. The tolerance of misalignment is a function of the focused beam diameter and to a lesser extend the joint design. To that end, control over the straightness of mating edges in the seam as well as collinearity of the primary/longitudinal axes of the shell 50 and support member 52 is desirable as seam welding is usually an autogeneous process that requires no added filler material during welding.

Figure 9B:
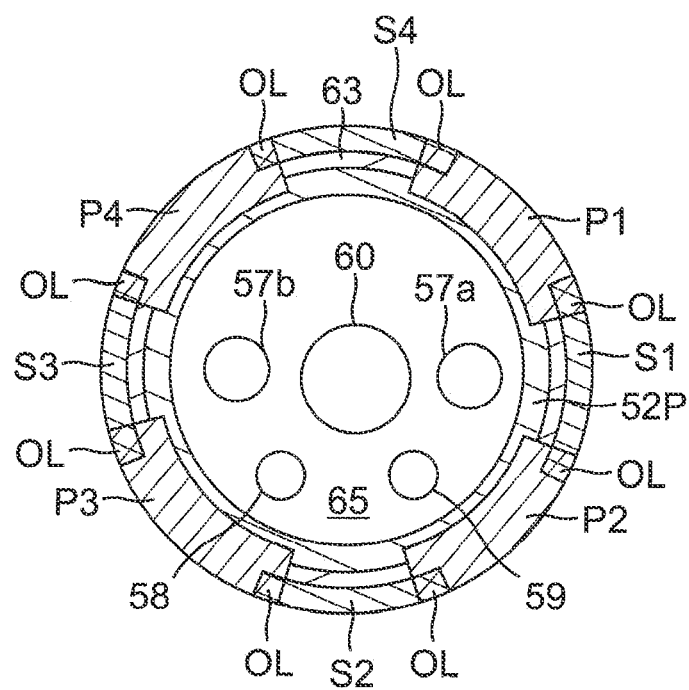
FIG. 9B is an end cross-sectional view of a tip electrode, in accordance with another embodiment.

The penetration weld 82 welds together the shell wall 63 of the shell 50 and the proximal portion 52P of the support member 52 (or "lap" joint) at a location distal of the ridge 67. The penetration weld may comprise a plurality of circumferentially-extending discontinuous segments P1-Pm. In the illustrated embodiment of FIG. 9A, m=2 such that the peripheral weld includes a first segment P1 and a second segment P2, each segment diametrically opposed to each other and extending between about 90-110 degrees, and preferably about 100 degrees, in arc length. In the illustrated of FIG. 9B, m=4 such that the seam weld 80 includes segments P1-P4, each at equidistance from adjacent segments and having the same circumferential length. The four segments form two pairs, each segment of a pair being diametrically opposed from its mate. It is understood that n at a minimum is 2 and may have a maximum that is equal to the total sum of the number of seam and penetration segments around the circumference divided by 2.

As shown in FIG. 10, the shell wall 63 is welded onto the proximal portion 52P in a radially top-bottom configuration by the penetration weld 82 which has a weld depth that penetrates the entire thickness of the shell wall 63 and into the support member 52. As understood by one of ordinary skill in the art, the penetration weld has a radial depth that sufficiently keyholes through the rim 55 and into the support member 52. In that regard, vertical tolerance (or depth of focus) relates to ensuring the focus spot at the joint has sufficient energy density to make a keyhole. The degree of air gap or fitment tolerance between the shell 50 and the support structure 52 is also important to assure that laser beam sufficiently couples the two components and keyholes through the rim 55 and into the support member 52.

As mentioned above, within each seam weld segment Si and each penetration weld segment Pi, the laser spot S has a predetermined circumferential overlap OL(c). At end portions of each seam and penetration weld segment Si and Pi, the end portions have a predetermined relative circumferential overlap OL (rc) between adjacent seam and penetration weld segments Si and Pi which may range between about 5-15 degrees in arc length and preferably about 10 degrees in arc length.

The laser spot S in the end portions also have an axial overlap OL(a) between adjacent seam and penetration weld segments Si and Pi which may range between about 50-80% and preferably about 60-70%. In accordance with a feature of the present invention, overlaps (axial and circumferential) between the seam weld segments and the penetration weld segments are kept to a minimum to avoid one weld damaging or otherwise weakening the integrity of the other weld while still providing dual failure mode in the tip electrode. In the illustrated embodiment, the penetration weld 82 is positioned about 0.002 inch distal of the seam 77. The seam weld is positioned such that the spot center is positioned distal to a parting line between the shell 50 and the support member 52 by a fixed amount.

The combination or "linking" of segments of seam weld segments Si and penetration weld segments Pi covers 360 degrees (or greater than 360 degrees if inclusive of one or more circumferential overlaps) in arc length circumferentially around the tip electrode such that the plenum chamber 51 has a fluid tight seal around the seam 77.

Figure 13:
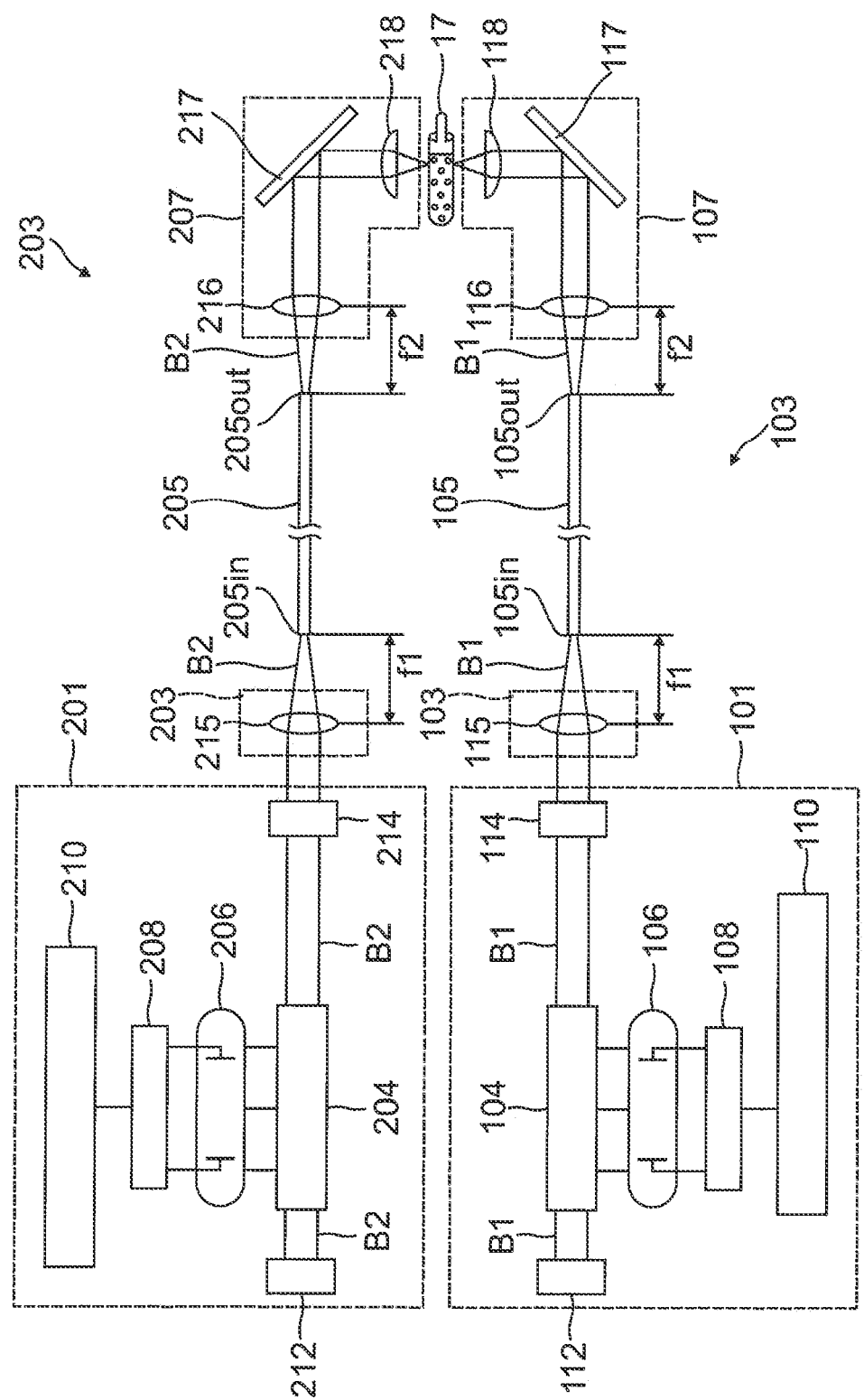
FIG. 13 shows a concept of a laser beam irradiation apparatus according to another embodiment.

In an alternate embodiment as shown in FIG. 13, a second laser beam irradiation apparatus 200 with a second laser beam generator 201 and a second optical unit 203, is used with the first laser beam irradiation apparatus 100 to provide separate processes for producing a separate second weld with both the first and second welds capable of meeting minimum tensile strength requirements. The second laser beam generator 201 and second optical unit 203 have components similar to those of the first laser beam generator 101 and the second optical unit 103, as described above, and thus are identified by similar reference numerals. In the illustrated embodiment, the first laser beam generator 101 and first optical unit 103 are configured to produce the penetration weld segments Pi on the tip electrode 17 and the second laser beam generator 201 and second optical unit 203 are configured to produce the seam weld segments Si on the tip electrode 17. Separate power supplies 108 and 208 and separate controllers 110 and 210 are provided.

It is understood that the present invention may include more than two independent welds and a variety of other weld configurations. The seam weld segments would be arrayed at about 120 degrees arc length or other sub-multiples 20 degrees arc length. Moreover, the seam and/or the penetration welds may be nonlinear, e.g., zigzag, in the circumferential direction, in order to manipulate surface area along the seam for improved loading. A third method of attachment may be provided in addition to the seam weld and the penetration weld provided that spacial requirements are satisfied.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings which are not necessarily to scale, but rather should be read consistent with and as support to the following claims which are to have their fullest and fair scope.

What is claimed is:

1. A catheter comprising:
   a catheter body;
   an intermediate section distal of the catheter body; and
   a distal section distal of the intermediate section, the distal section comprising a tip electrode and a non-conductive covering disposed between the tip electrode and the intermediate section, the tip electrode comprising:
   a shell piece having a hollow cylindrical body with an open proximal end defined by a peripheral rim,
   a support member piece having a generally cylindrical body, including a proximal portion and a distal portion, and an annular ridge projecting from an outer surface of the proximal portion and,
   a joint seam that is formed by an abutment of the annular ridge and the peripheral rim and a weld, the weld comprising at least one seam weld and at least one penetration weld.

2. The catheter of claim 1, in which the covering comprises a connector tubing that houses a position sensor and through which wires and an irrigation tubing connect to the tip electrode.

3. The catheter of claim 1 in which the shell piece includes a domed atraumatic distal end.

4. The catheter of claim 1, in which the distal portion of the support member piece and a distal segment of the proximal portion of the support member piece are disposed inside the shell.

5. The catheter of claim 1, in which the proximal portion of the support member piece has a larger diameter than the distal portion of the support member piece.

6. The catheter of claim 5, in which a distal segment of the proximal portion of the support member piece contacts an inner surface of the shell piece in an interference fit.

7. The catheter of claim 6, in which the shell piece has a thickness and the ridge has a height that is equal to the thickness.

8. The catheter of claim 7, in which the proximal portion of the support member comprises a plurality of off-axis axial holes.

9. The catheter of claim 1, in which the seam weld comprises a plurality of seam-weld segments including a first seam-weld segment and a second seam-weld segment, and the penetration weld comprises a plurality of penetration-weld segments including a first penetration-weld segment and a second penetration weld-segment.

10. The catheter of claim 9 the plurality of penetration-weld segments weld together the shell piece and the distal segment of the proximal portion of the support member.

11. The catheter of claim 10, in which the plurality of seam-weld segments and the plurality of penetration-weld segments cover 360 degrees in arc length circumferentially around the shell.

12. The catheter of claim 11, in which the which the plurality of seam-weld segments and the plurality of penetration-weld segments form a fluid-tight seal between the support member and the shell piece.

13. The catheter of claim 12, in which the first seam-weld segment overlaps the first penetration-weld segment to define an overlap.

14. The catheter of claim 13, in which the overlap comprises a circumferential overlap.

15. The catheter of claim 14, in which the circumferential overlap comprises between 5 to 15 degrees in arc length.

16. The catheter of claim 15, in which the circumferential overlap comprises about 10 degrees in arc length.

17. The catheter of claim 16, in which the overlap comprises an axial overlap.

18. The catheter of claim 17, in which the axial overlap ranges between 50% and 80%.

19. The catheter of claim 18, in which the axial overlap ranges between 60% and 70%.

\* \* \* \* \*